(12) United States Patent
Craine (10) Patent No.: US 6,228,040 B1
(45) Date of Patent: May 8, 2001

(54) METHOD AND APPARATUS FOR DIAGNOSIS OF IRRITABLE BOWEL SYNDROME

(75) Inventor: Brian L. Craine, Fairfax, CA (US)

(73) Assignee: Western Research Company, Inc., Tucson, AZ (US)

( * ) Notice: Subject to any disclaimer, the term of this patent is extended or adjusted under 35 U.S.C. 154(b) by 0 days.

(21) Appl. No.: 09/362,387

(22) Filed: Jul. 28, 1999

Related U.S. Application Data (60) Provisional application No. 60/095,326, filed on Aug. 4, 1998.

(51) Int. Cl.⁷ .................................................. A61B 7/00
(52) U.S. Cl. ............................................................ 600/586
(58) Field of Search ................................... 600/586, 300

(56) References Cited

U.S. PATENT DOCUMENTS

| | | | |
|---|---|---|---|
| 4,720,866 | 1/1988 | Elias et al. | 381/67 |
| 4,770,189 | * 9/1988 | Shyu | 600/586 |
| 4,792,145 | 12/1988 | Eisenberg et al. | 128/715 |
| 4,991,581 | 2/1991 | Andries | 128/715 |
| 5,025,809 | 6/1991 | Johnson et al. | 128/715 |
| 5,218,969 | 6/1993 | Bredesen et al. | 128/710 |
| 5,301,579 | 4/1994 | Taylor | 128/773 |
| 5,928,156 | 7/1999 | Krumbiegel et al. | 600/529 |

OTHER PUBLICATIONS

"Bowel–Sound Signal Enhancement Using Adaptive Filtering, Separating Heart Sounds from Gastrointestinal Acoustic Phenomena", by Hussein A. Mansy and Richard H. Sandler, IEEE Engineering in Medicine and Biology, Nov./Dec. 1997, pp. 105–117.

"Computerized Phonoenterography: The Clinical Investigation of a New System", by Michael Sugrue and Michael Redfern, J Clin Gastroenterol, vol. 18, No. 2, 1994, pp. 139–143.

"Gastrointestinal Sounds and Migrating Motor Complex in Fasted Humans", by Tomomasa et al., The American Journal of Gastroenterology, vol. 94, No. 2, 1999, pp. 374–381.

* cited by examiner

Primary Examiner—Cary O'Connor
Assistant Examiner—Brian Szmal
(74) Attorney, Agent, or Firm—Cahill, Sutton & Thomas P.L.C.

(57) ABSTRACT

A protocol for the recording of bowel sounds, a computerized algorithm for recognizing the start and stop time of bowel sounds in the digital sound recordings, metrics that can be calculated from the start and stop times and limits of these metrics which can be used to categorize individuals with respect to medical conditions which effect the gastrointestinal tract. The use of these methods and values allows for the diagnosis of certain gastrointestinal syndromes or diseases with a high degree of accuracy in a manner not previously possible.

40 Claims, 3 Drawing Sheets

METHOD AND APPARATUS FOR DIAGNOSIS OF IRRITABLE BOWEL SYNDROME

CROSS REFERENCE TO RELATED APPLICATION

This application claims the benefit of prior filed co-pending U.S. Provisional Application Serial No. 60/095,326, filed Aug. 4, 1998, entitled "DIAGNOSTIC TEST FOR GASTROINTESTINAL COMPLAINTS" by Brian L. Craine.

BACKGROUND OF THE INVENTION

The invention relates to using a computerized analysis of bowel sounds recorded using an electronic sound input device to diagnose gastrointestinal complaints of pain, bloating, or alteration of bowel habits, with emphasis on the diagnosis of irritable bowel syndrome.

Irritable bowel syndrome is characterized by bowel irregularity (constipation and/or diarrhea), gaseous distention and abdominal pain. Irritable bowel syndrome is the most common gastrointestinal complaint for which patients seek medical care, accounting for 30 to 50 percent of the gastrointestinal complaints that bring patients to a physician. Various studies indicate that patients with irritable bowel syndrome constitute a large portion of a typical family physician's practice and account for more than 25% of all gastrointestinal referrals. Irritable bowel syndrome is listed as a primary diagnosis in about 96,000 patients per year treated in nonfederal hospitals, and the disorder was considered a secondary diagnosis in another 85,000 patients. Most patients with gastrointestinal complaints are subjected to a battery of laboratory studies. These usually include sigmoidoscopy, complete blood count, erythrocyte sedimentation rate, serum electrolytes, liver function tests, urinalysis, and stool examination for occult blood and parasites. For a patient with chronic or recurring symptoms, endoscopy or radiographic contrast evaluations can be performed (but should not be repeated unless there is objective evidence of a change in the clinical condition, such as blood in the stool).

Since most patients with irritable bowel syndrome do not require hospitalization, these figures indicate only a fraction of the social and economic burden this condition places on patients and the health care system.

In western societies, irritable bowel syndrome occurs twice as often in women as in men. About half of the patients are first seen for this condition before they reach 35 years of age. Various studies indicate that almost half of the patients are between the ages of 35 and 49, although symptoms usually begin much earlier and are likely to continue throughout life. The true prevalence of irritable bowel syndrome may be reflected in several non-patient surveys in which as much as 20 percent of the general population reported symptoms consistent with this disorder. The majority of these people do not seek medical assistance, although it is possible that their symptoms could be alleviated through education, simple methods of stress reduction, and dietary changes.

In some patients with the irritable bowel syndrome, the intraluminal contents appear to have an unusually rapid transit time through the length of the small intestine and colon. The syndrome is a well-recognized clinical entity but does not yet have a pathophysiological counterpart because no etiologic agents have been identified and no structural or biochemical defect has been determined. Indeed, other terms for the disease include spastic colitis, mucous colitis, and the irritable colon syndrome. Affected patients generally complain of generalized abdominal discomfort. Other common symptoms include audible bowel noises, cramping abdominal pain, urgency to defecate, and the passage of loose stools, often covered with mucus but free of blood.

The symptoms of irritable bowel syndrome may be exacerbated by any factor that increases gastrointestinal motility, such as ingestion of large or fatty meals (gastrocolic reflex), medication, hormonal changes that occur at menses (increased prostaglandin E2 release), and psychological stress. Foods and beverages that produce gas (e.g., beans, cabbage) or stimulate intestinal action (e.g., caffeinated beverages) may also exacerbate this disorder.

The differential diagnosis should include other conditions that produce similar changes in bowel habits, particularly ulcerative colitis, granulomatous enteritis (Crohn's disease), and infectious diseases of the small and large intestines. (The term "differential diagnosis" refers to a group of most likely diagnoses that have the same or similar symptoms and therefore could be confused with one another.) Lactase deficiency is often associated with similar symptoms, but these disappear when the offending disaccharide is removed from the diet. Low-grade, intermittent mechanical obstruction of the small intestine may produce symptoms that are very difficult to distinguish from those of the irritable bowel syndrome. The diagnosis must always be based on exclusion of other possible illnesses, and the physician should be on the alert for changes in symptoms which may indicate some other illness, such as a serious organic disease.

The irritable bowel syndrome is understood as a motility disorder involving the small and large intestines. Although the human intestine is relatively inaccessible to investigation, several physiologic characteristics have been discovered that distinguish patients with irritable bowel syndrome from healthy individuals. Abnormalities in colonic motor activity noted in irritable bowel syndrome include an altered gastrocolonic motor response, an exaggerated colonic motor response to pain, stress, or hormonal stimulation, and increased sensation and motor activity in response to balloon distention of the rectosigmoid region. Similarly, abnormalities in motor activity of the small bowel noted in irritable bowel syndrome include exaggerated motor response to fatty meals, ileal balloon distention, or hormonal stimulation, altered ileocecal transit and an increase in motility patterns during fasting. These basic studies of motility have recently been extended using 24-hour ambulatory monitoring systems measuring motility in the small bowel. These studies confirm the presence of dysmotility in irritable bowel syndrome patients compared to normal patients.

Previous methods of performing motility studies involved colonic intubation with a multi-lumen catheter with side hole manometric ports after colonic lavage (e.g. with a high osmolarity solution, such as, GoLYTELY). These studies are particularly difficult to perform when evaluating treatment strategies for irritable bowel syndrome. The nature of the measurements have restricted application of these methods to small numbers of patients, and the overlap in the measurements between normal and irritable bowel syndrome populations is great, further complicating analysis of the studies.

SUMMARY OF THE INVENTION

Accordingly, it is an object of the invention to provide a test and positive diagnosis technique specific to irritable bowel syndrome which require only a few minutes to perform in a usual examining room setting.

It is another object of the invention to provide an accurate diagnosis of irritable bowel syndrome in less than 20 minutes while the patient is still at the site of care.

It is another object of the invention to provide a non-invasive diagnostic method for irritable bowel syndrome.

It is another object of the invention to provide a diagnosis technique that is sensitive and specific for diagnosing irritable bowel syndrome.

It is another object of the invention to provide a positive diagnosis, rather than a diagnosis based on exclusion of other possible illnesses, for patients with irritable bowel syndrome.

It is another object of the invention to provide a method that could be applied to the diagnosis of other gastrointestinal diseases than irritable bowel syndrome by computer analysis of bowel sound patterns.

It is another object of the invention to provide a positive test and diagnosis for gastrointestinal complaints to more accurately guide the choice of medications for some patients.

It is another object of the invention to provide a compatible diagnostic test method for irritable bowel syndrome that can be accomplished with any of a variety of common computers that may be available in a typical health care setting.

Briefly described, and in accordance with one embodiment thereof, the invention provides a system and method for determining quantitative metrics for the characterization of bowel sound recordings from the human abdomen so as to allow a positive diagnosis of the presence or absence of irritable bowel syndrome in a patient. The system includes an electronic microphone including a sound conducting diaphragm adapted to provide good acoustic contact with an abdomen of the patient. A medium, such as a wire cable, is adapted to communicate a signal produced by the electronic microphone in response to bowel sounds in the patient to an analog-to-digital conversion circuit. A digital computer is adapted to receive digital information representative of a first, and optionally a second sequence of bowel sounds of the patient in a fasting condition and in a fed condition, respectively, from the analog-to-digital conversion circuit. The digital computer executes a program to produce a first group of digital numbers representing times of occurrence of fasting bowel sounds having at least a first predetermined amplitude and store the first group of digital numbers as a first table, and, if fed bowel sounds have been produced, to produce a second group of digital numbers representing times of occurrence of fed bowel sounds having at least a second predetermined amplitude and store the second group of digital numbers as a second table. The computer computes a first number representative of a frequency of the fasting bowel sounds, and if the frequency is greater than a predetermined threshold, a diagnosis is made of irritable bowel syndrome in the patient. If fed bowel sounds have been produced, the computer computes a second number representative of a frequency of the fed bowel sounds and computes a first ratio representative of a predetermined relationship between the first number and the second number, and a diagnosis is made of irritable bowel syndrome if the ratio bears a predetermined relationship to a predetermined threshold.

DETAILED DESCRIPTION OF THE PREFERRED EMBODIMENTS

In accordance with the present invention, I have found that computer based quantitative analysis of sounds produced by the gastrointestinal tract provide a useful method for evaluating patients with dysmotility syndromes. (The term "motility" refers to how fast material moves through the intestines as a result of contractions of the intestines.) Such bowel sounds can be measured in a noninvasive manner. Noninvasive methods are more clinically practical than invasive techniques. While physicians have long been taught to listen for bowel sounds, the sounds that I found to be useful are not readily detectable by merely using a standard stethoscope. Instead, a complex, quantitative analysis of the sounds detected over a period of time by an electronic stethoscope or the like are required.

Using a sensitive electronic stethoscope, sounds with an average duration of about 23 msec and a predominant frequency of 300 Hz can be detected. Using these parameters to develop a computer algorithm for quantitative analysis of the bowel sound recordings, I have found that the bowel sounds occur at an average of every 1931 milliseconds (with a standard error of 365 milliseconds) in normal individuals, and at an average of every 452 milliseconds (with a standard error of 35 milliseconds) in patients with irritable bowel syndrome when the patients have fasted for at least 2 hours.

However, following a test meal that stimulates the gastrocolic reflex, the sounds occur at an average of every 429 standard milliseconds in the normal individuals (with a standard error of 81 milliseconds) and at an average of every 400 milliseconds in patients with irritable bowel syndrome.

Thus, in both normal patients and irritable bowel patients bowel sounds consistently are about the same, at a relatively high frequency, soon after consuming a test meal. However, the frequency of the bowel sounds of normal patients who have fasted for a few hours are very low compared to the frequencies of the bowel sound of irritable bowel patients who have fasted for several hours. This finding and technique provide a new practical and positive test for distinguishing between irritable bowel patients and others. (As indicated above, irritable bowel syndrome has previously been a diagnosis only by exclusion of other possible illnesses.)

I have also found that the frequency of bowel sounds of patients who have fasted is significantly different for patients with Crohn's disease and those with irritable bowel syndrome. This is important because Crohn's patients are sometimes erroneously diagnosed as irritable bowel patients, which delays proper treatment. The present invention could help to alleviate this problem.

The present invention provides 1) a noninvasive means to evaluate the gastrointestinal tract, 2) an algorithm for quantitative evaluation of recorded bowel sounds, 3) established cutoff values of the sound-sound intervals, or other metrics described herein for distinguishing between normal subjects and irritable bowel subjects, and 4) established cutoff values of the sound-sound intervals, or other metrics for distinguishing between Crohn's patients and irritable bowel patients.

Figure 1:
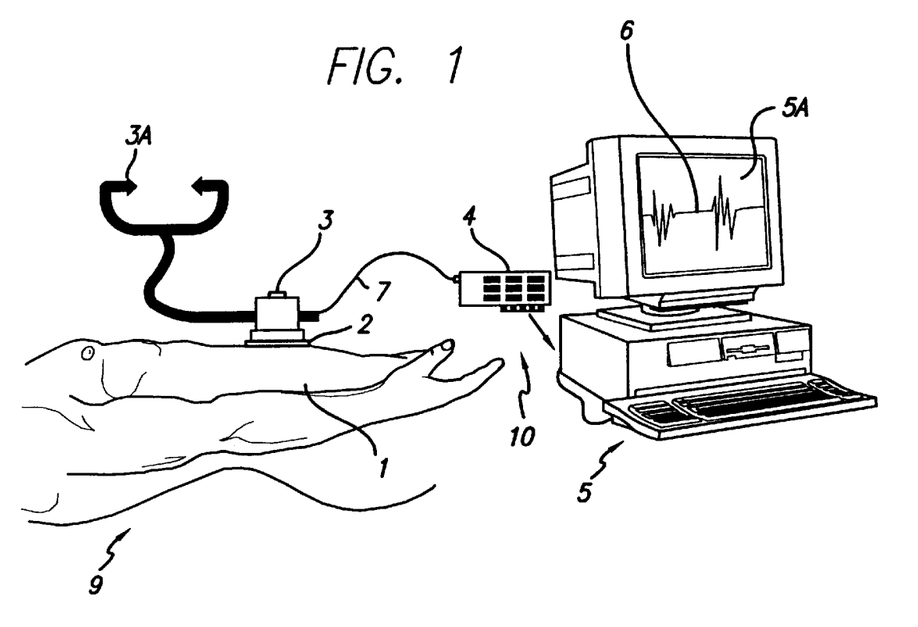
FIG. 1 is a partial perspective view diagram of the preferred testing equipment used in the present invention and also a portion of a subject's body.

Referring now to FIG. 1, the patient 9 is instructed to fast for 2 hours prior to examination. The patient 9 then lies horizontal with electronic stethoscope 3 placed in contact with the right lower quadrant of the patient's abdomen 1. Electronic stethoscope 3 can be a model ES-120, available from JAC Instrument Co., Van Nuys, Calif. Acoustic contact is ensured by coating the diaphragm of electronic stethoscope 3 with a sound conducting gel, both to provide the good acoustic contact and to reduce artifactual noise due to friction. Electronic stethoscope 3 is held in contact with the abdomen 1. The resulting output signal from the electronic stethoscope 3 travels over wire cable 7 to the input port of a sound card 4 in personal computer 5. Sound card 4 can be a model SOUNDBLASTER 16, available from Creative Labs, and actually is installed in personal computer 5 (rather than outside of it as shown for illustrative effect in FIG. 1). A model 7500 SAGER lap top computer including a 486DX2 microprocessor can be used. The bowel sound signal then is recorded as a digitized sound file stored in the computer, and is displayed as a bowel sound signal 6 on the monitor 5A of computer 5.

The bowel sounds are digitized and recorded as eight bit bytes at a digital sampling rate of 11,025 Hz for a two minute period, to produce a "fasting patient bowel sound file", referred to herein simply as a "fasting sound file".

Optionally, the subject then ingests a 240 calorie, 237 milliliter test meal, which can be SUSTACAL™ which consists of sufficient volume to stimulate the gastrointestinal tract. Approximately ten to fifteen minutes later a similar second two minute recording of the patient's bowel sounds is obtained to produce digitized "fed patient bowel sound file data", referred to simply as a "fed sound file". The fasting sound file is stored in the memory of computer 5, and if a fed sound file is also provided, it also is stored in the memory of computer 5.

The fasting sound file, and also the optional fed sound file if it is used, then are analyzed by computer 5 to determine the "start time" and the "stop time" of each "presumed bowel sound". This is accomplished by inputting the sound waveform data, which is a time series of digitized sound intensities, to a recursive digital infinite impulse response (IIR) band pass software filter executed by computer 5. The fasting sound file, and the fed sound file if it is used, are filtered by the IIR digital bandpass filter to process the raw sound file data. An algorithm subsequently described with reference to FIGS. 2A and 2B "thresholds" the band pass filtered signal amplitudes over a moving window average to produce a first table of "fasting bowel sound start times" and fasting bowel sound stop times" of successive presumed bowel sounds from the fasting sound file. If applicable, the algorithm of FIGS. 2A and 2B also produces a second table of "fed bowel sound start times" and "fed bowel sound stop times" of the successive bowel sounds from the fed sound file.

Figure 2A:
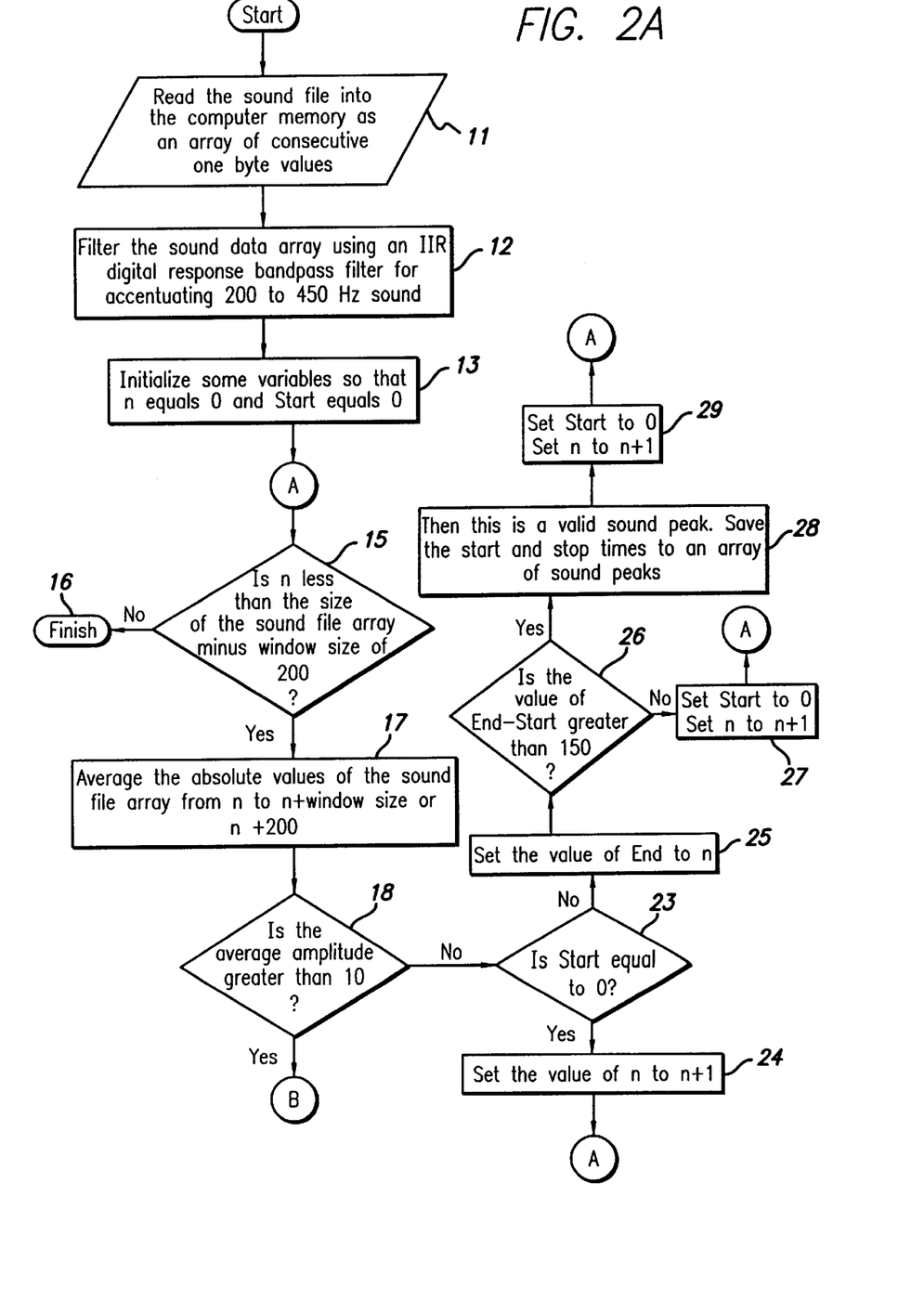
FIGS. 2A and 2B constitute a flow chart of a computer program that performs band pass filtering and analysis of data in bowel sound files to detect the start times and stop times of detected bowel sounds.
Figure 2B:
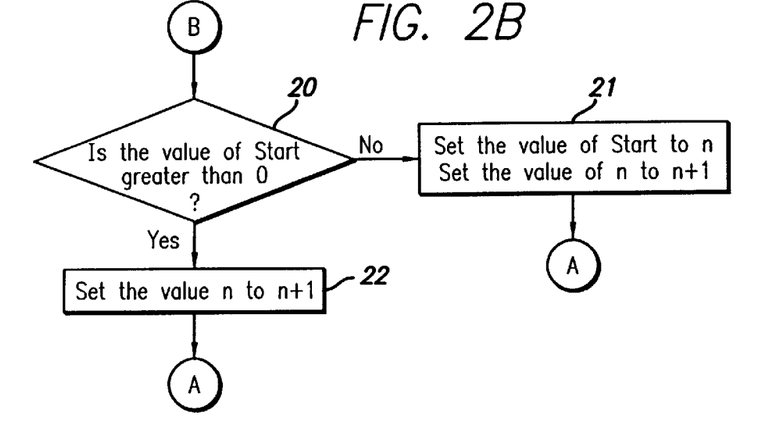

The start and stop times of sequential bowel sounds are determined for both the fasting sound file and the fed sound file using the computerized analysis algorithm illustrated in FIGS. 2A and 2B. Table 1 includes a code in the C/C++ language for a routine that performs the analysis of the sound file to detect the start and stop times of both fasting bowel sounds, and fed bowel sounds if they are used, according to the flow chart of FIGS. 2A and 2B.

Before describing the algorithm of FIGS. 2A and 2B by computer 5, the above mentioned recursive IIR filter which is executed by the algorithm will be described. The general form of such a recursive digital IIR filter is:

$$y_n = \sum_{k=0}^{M} c_k x_{n-k} + \sum_{j=1}^{N} d_j y_{n-j}, \qquad \text{(Eq. 1)}$$

where $y_n$ is the $n^{th}$ output value, $x_{n-k}$ is the n-$k^{th}$ original input value, c and d are coefficients. This IIR filter produces each new output value from the current and M previous input values and from its own N previous output values, N and M being integers. (IIR recursive filters generally have a superior performance compared to nonrecursive filters using the same number of coefficients. However, while nonrecursive filters are always stable, recursive filters can be unstable, depending on the choice of the d coefficients.)

The digital IIR bandpass filter is applied to data sequentially output from the fasting and fed bowel sound files to reduce background sound noise. This involves calculating a filtered signal series $y_n$ from the original sound signal series $x_n$, where n is the integer numbered position in the series, according to above Eq. 1, where:

$y_n$ is the $n^{th}$ filtered signal value, $x_{n-k}$ is the n-$k^{th}$ signal value of the original sound file being filtered, M is 3, N is 2, a=tan(($\pi$*200)/(sampling frequency, e.g.,11,025)), b=tan(($\pi$*450)/(sampling frequency, e.g.,11,025)), c0=-(b/((1+a)×(1+b)), c1=0,c2=-c0, d1=(((1+a)*(1-b))+((1-a)*(1+b)))/((1+a)*(1+b)), and d2=-(((1-a)*(1-b))/((1+a)*(1+b))).

Since I had previously determined that bowel sounds generally have a predominant frequency of approximately 300 Hz and that the background sounds detected by electronic stethoscope 3 generally have predominant frequencies outside of the range between 200 Hz and 600 Hz, I designed a stable 200 to 450 Hz recursive IIR band pass filter according to Eq. 1 to both eliminate such background sound and also leave the meaningful measured bowel sounds only slightly diminished in amplitude. This was achieved using only 5 coefficients in Eq. 1, which allows use of a fast algorithm to implement the recursive IIR filter of above Eq. 1 so as to greatly reduce the background noise in the sampled sound waveform to zero or nearly zero.

A moving recursive "window" consisting of 200 consecutive data points of a bowel sound file is analyzed to determine an average bowel sound signal intensity. My analysis of a large number of such bowel sound recordings has revealed that the average signal intensity of a 200 point window for background sounds other than bowel sounds typically does not exceed a threshold value of 10. If the present output of the IIR filter of Eq. 1 equals or exceeds that "average bowel sound signal intensity threshold" of 10, then a "bowel sound start time" is set, to mark the beginning of a "presumed bowel sound". When the intensity of that sound signal after filtering by the IIR filter ceases to exceed the average signal intensity threshold of 10, an end time or "bowel sound stop time" of the presumed bowel sound is set. Such start times and stop times of all consecutive presumed bowel sounds contained in the fasting bowel sound file and the fed bowel sound file are stored in first and second corresponding tables, respectively, hereinafter also referred to as first and second sound tachograms.

With the foregoing general description in mind, the flow chart of FIGS. 2A and 2B will be described. This flow chart represents the algorithm for determining the above mentioned start times and stop times for presumed bowel sounds by analysis of a standard 8-bit sound wave file.

The program of FIGS. 2A and 2B begins in block 11, wherein the previously digitized and stored fasting sound file is read into the memory of computer 5 (FIG. 1) as an array of consecutive 1-byte values each representing the amplitude of a consecutive sound sample, respectively. The program then goes to block 12 and filters the consecutive amplitude samples using an infinite impulse response (IIR) band pass filter that passes sound in the 200 to 450 Hertz frequency range.

The program then goes to block 13 and initializes a variable n (which is the number of the present pass through the analysis loop starting at point A) to be equal zero and a variable START to be equal to zero. The program then goes to decision block 15 and determines if the variable n is less than the size of the sound file minus the window size, which for this example is selected to be 200 bytes, i.e., 200 consecutive sound amplitude samples. If this determination is negative, then the program execution is complete, as indicated by label 16. The result of execution of the program of FIGS. 2A and 2B constitutes the array of start times and stop times assigned in block 28.

The start times and stop times are set in milliseconds from the beginning of the corresponding sound file, in which each entry includes a digital sound signal amplitude and a time of occurrence of that sample.

However, if the determination of decision block 15 is affirmative (i.e., if the program is still operating within a "window" moving through the sound file array) the program goes to block 17 and sums the absolute values of the amplitudes constituting the sound file bytes within the "window" of the sound file; the size of the window can be 200 bytes. The program then goes to decision block 18 and determines if the average of the sum of sound amplitudes computed in block 17 is greater than a predetermined amplitude, for example 10. If this decision is affirmative, the program then enters decision block 20 and determines if the value of the variable START is greater than zero, i.e., if START has been set yet. If this determination is affirmative, the program goes to block 22, increments the variable n, reenters decision block 15 at A, and repeats the analysis loop.

If the determination of decision block 20 is negative, the program goes to block 21, sets the variable START to the present value of the variable n to indicate the beginning of a possibly significant group of sound amplitudes, increments n, and then reenters the analysis loop at the entry point A of decision block 15.

If the determination of decision block 18 is that the average amplitude determined in block 17 is not greater than 10, the program goes to decision block 23 to determine if the variable START is equal to zero, i.e., to determine if START has not already been set. If a value of START has not yet been set, the program increments n in block 24 and reenters point A of the analysis loop. If the determination of decision block 23 is negative, a value of START already has been set, so the program enters block 25 and sets the value of the variable END to the present value of n.

The program then goes to decision block 26 and determines if the duration of time in which the average of the sum of sound amplitudes computed in block 17 exceeded the value 10 (i.e., the value of END minus START) is greater than a certain time duration corresponding to, for example, 150 samples. If this determination of decision block 26 is affirmative, the program goes to block 28 and concludes that the amplitude computed in block 17 has been greater than the predetermined threshold value of 10 for a long enough time to represent a valid sound peak; the program then saves the present values of START and END in an array of sound peak values. The program then goes to block 29, resets START to 0 increments n and then reenters the analysis loop at the entry point A of decision block 15. If the determination of decision block 26 is negative, the program goes to block 27 and resets START to 0, increments n, and returns to the entry point A of decision block 15 to re-execute the analysis loop.

After the first and second tables of start and stop times for each presumed bowel sound for both the fasting bowel sound file and the fed bowel sound file have been generated by computer 5 in accordance with the algorithm of FIGS. 2A and 2B, the next step is to determine which presumed bowel sounds are "valid bowel sounds".

This is accomplished by computing the power spectra of the original time series of digital bowel sound data so as to determine if it is within the 200–450 Hz range. The original non-filtered data points between each pair of start and stop times within each of the first and second tables represent a time series data stream which is used to calculate an associated power spectrum. This can be accomplished using standard fast Fourier transform (FFT) algorithms such as published in the "Numerical Recipes in C: The Art of Scientific Computing" by WH Press (Cambridge University Press, 1988).

Using the computed power spectra, each presumed bowel sound is then selected to be a valid bowel sound if at least 15% of the power spectra for that presumed bowel sound is between 200 and 450 Hz. Otherwise that presumed bowel sound is deleted from the two tables of bowel sound start times and stop times. What is left in the two tables then constitutes two tachograms, one tachogram including the start times and stop times of each valid bowel sound in the fasting bowel sound file, and the other tachogram including the start times and stop times of each valid bowel sound in the fed bowel sound file, if fed bowel sounds are used.

A practical advantage of this check is that it is possible to reduce the intensity criteria to a point that the described algorithm allows very subtle sounds to be detected, including some that are not valid bowel sounds. Then such sounds which are not valid bowel sounds are eliminated by the final step of determining the power spectra. This makes the overall detection of valid bowel sounds more sensitive.

After the first and second tables of valid bowel sound start times and stop times are obtained, they are used to calculate the following diagnostic metrics, which include (1) the average sound-sound interval of the fasting sound file, (2) the standard deviation of the sound-sound interval of the fasting sound file, (3) the ratio of the sound-sound interval for the fasting sound file to that of the fed sound file if one is used, and (4) the ratio of the standard deviation of the sound-sound interval for the fasting sound file to that of the fed sound file if one is used.

These diagnostic metrics are calculated as:

$$\overline{S}_{fasting} = \frac{\sum_{x=1}^{x=n}\left(start_{x+1}^{fast} - start_{x}^{fast}\right)}{(n-1)} \quad \text{(Eq. 2)}$$

where $\overline{S}_{fasting}$ is the average fasting sound-sound interval and n is the total number of sounds detected in the fasting sound file.

The ratio of the fasting to fed sound-sound interval is:

$$S - S \text{ ratio} = \frac{\overline{S}_{fast}}{\overline{S}_{fed}}, \quad \text{(Eq. 3)}$$

The foregoing calculated diagnostic metrics are then compared with those values obtained with previously diagnosed patients to determine if the patient has irritable bowel syndrome. My experience indicates that if the $\overline{S}_{fasting}$ is less than 640 milliseconds the test would indicate that the patient has irritable bowel syndrome, or if the sound-sound interval ratio is less than 1.8 the test would indicate that the patient has irritable bowel syndrome.

The normal values of the average time between sounds during the fasting state and the ratio of the fasting average time to the fed average time indicate that an average fasting sound interval of less than 640 milliseconds, or a value of the foregoing ratio of less than 1.8 if fed bowel sounds are used, are highly predictive of irritable bowel syndrome. The values determined for the present patient are compared with these values to determine if the patient has irritable bowel syndrome. If the sound-sound interval for a fasting sound file for the present patient is less than 640 milliseconds, the test result indicates, with a sensitivity of 94.4%, a specificity of 93.3%, and a positive predictive value of 86%, that the patient has irritable bowel syndrome. (Clinical tests are usually characterized as to how "sensitive" they are and how "specific" they are as a measure of how effectively they result in a correct diagnosis of a particular condition or ailment.)

Thus, this invention can be used to determine an objective indication of the medical condition that has been commonly referred to as irritable bowel syndrome. The inexpensive and non-invasive computerized time series analysis of bowel sounds provides to healthcare workers, for the first time, a practical test with a positive quantitative result that distinguishes irritable bowel syndrome patients from subjects not having irritable bowel syndrome. The invention has the further advantage that it may be easily used during a routine medical examination.

In accordance with a further embodiment of the invention, it is possible to use the sound tachograms derived from multiple simultaneous recordings of bowel sounds from three or more different electronic stethoscopes to determine the locations of the individual bowel sounds. The location of each sound can be determined by triangulation of the sound intensities measured at each of the electronic stethoscopes after digital filtering as described above. This additional bowel sound mapping information may be useful in increasing the specificity of the bowel sound analysis to particular diseases. For example, it appears that patients with irritable bowel syndrome have a higher percentage of bowel sounds that originate from the mid or left abdominal region than do normal individuals.

Figure 3A:
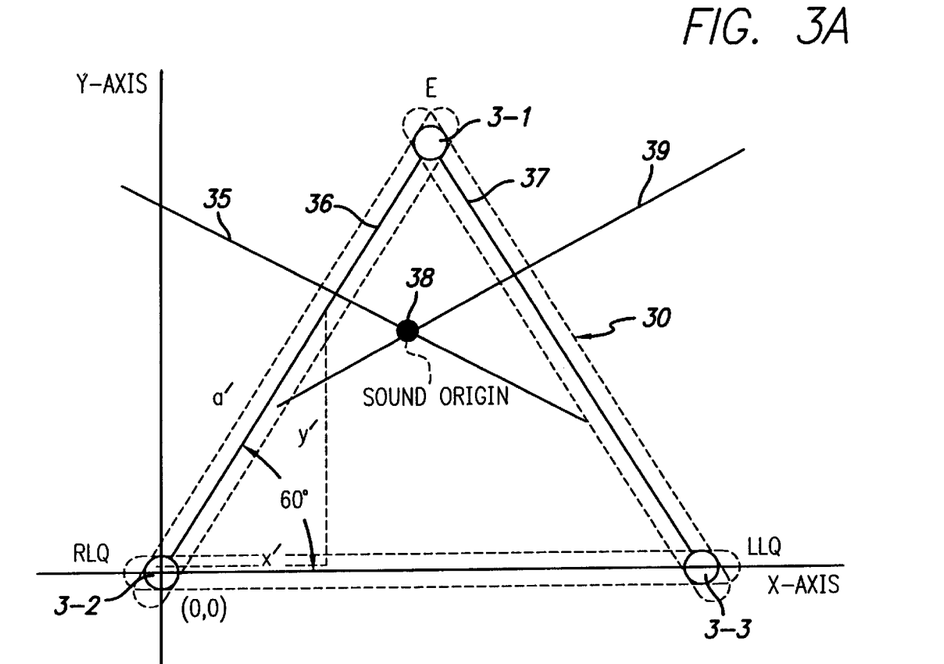
FIG. 3A is a diagram illustrating a bracket holding three electronic stethoscopes and is useful in explaining how the precise locations of bowel sounds are determined using the three electronic stethoscopes, to further aid in accurate, positive diagnosis of irritable bowel syndrome and other gastrointestinal ailments.
Figure 3B:
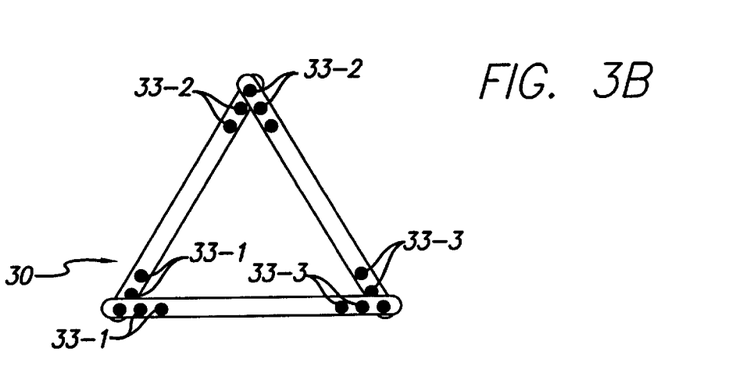
FIG. 3B is a top view of the bracket indicated in dotted lines in FIG. 3A.
Figure 3C:
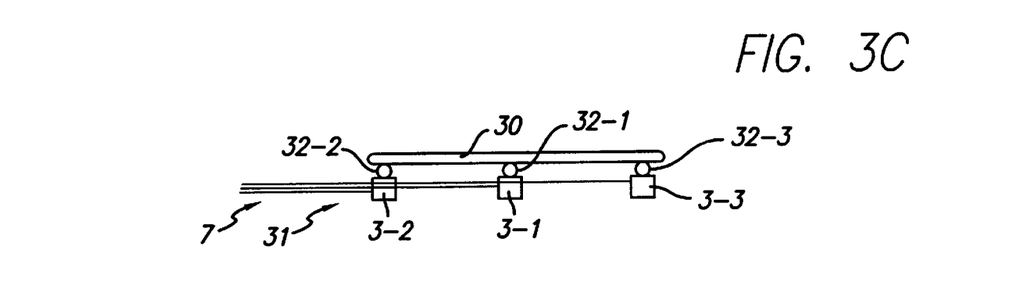
FIG. 3C is a side view of the bracket shown in FIG. 3B.

Referring to FIGS. 3A–3C, bowel sound mapping is accomplished by means of a frame 30 that holds three electronic stethoscope heads 3-1, 3-2 and 3-3 in fixed geometrical positions relative to each other by means of three ball joints 32-1, 32-1, and 32-3, respectively. Each of the three ball joints can be attached to various locations of frame 30 by connecting it to any of sockets 33-1, 33-2, or 33-3 in frame 30. The distances between the three stethoscope heads are equal, so that the heads form the vertices of an equilateral triangle with all three vertex angles equal to sixty degrees. The distance of a bowel sound generated between any two pairs of the stethoscope heads 3-1, 3-2 and 3-3 is assumed to be equal to the relative intensity of that bowel sound as measured by the two stethoscope heads. For example, if the bowel sound were of equal intensity at two of the stethoscope heads, the source of the bowel sound would be located on a line half way between the two stethoscope heads.

Since the geometry of the arrangement of the stethoscope heads is known, it is possible to define an equation for that line between any two pairs of stethoscope heads. Determination of two such lines allows for the calculation of the intersection point between the two lines, which is the point at which the sound must have originated. We have two equations with two unknowns, the x and y coordinates of the sound, which can be easily solved by any of the methods used to solve simultaneous equations.

In this embodiment of the invention the bowel sound mapping is accomplished by simultaneously recording the bowel sounds from three stethoscope heads held 11 centimeters apart with a sixty degree angle between each of the stethoscope heads 3-1, 3-2 and 3-3 which also are held in contact with the surface of the patient's abdomen as shown in FIG. 1. A first head 3-1 is placed just below the xiphoid and referred to as the epigastric or E head, a second head 3-2 is placed in the right lower quadrant and is referred to as the RLQ head, and a third head 3-3 is placed in the left lower quadrant and is referred to as the LLQ head. The simultaneous sound recordings are analyzed by the above described method to produce a sound tachogram for each of the sound files. The start and stop times listed in the sound tachogram are then used to define the times of the bowel sound. The sound intensity of the corresponding bowel sound is determined for each of the three sound files by summing the absolute value of the recorded value of the respective sound waves between the start and stop times of each sound. This provides a list of sound intensities detected from each stethoscope for each detected sound.

The distance of the sounds between the epigastric head 3-1 and the RLQ head 3-2 is calculated as $$a_i = E_i/(RLQ_i + E_i), \quad \text{(Eq. 4)}$$

where the subscript i indicates the intensity measured at the indicated stethoscope head. This $a_i$ value can be used to calculate the x and y coordinate of one point on the line upon which the sound must have originated with the Cartesian coordinates defined by the plane of the stethoscopes heads 3-1, 3-2 and 3-3 and the origin being the point at which the RLQ head 3-2 is located (i.e., the point where x=0 and y=0). The x' and y' coordinates are calculated as:

$$x' = a_i \cos(60°) \text{ and } y' = a_i \sin(60°) \quad \text{(Eq. 5 and 6)}$$

The slope m of the line 35 on which the sound originates is the inverse of the slope of the line 36 between the two heads 3-1 and 3-2 and is therefore:

$$m = 1/\tan(60°) \quad \text{(Eq. 7)}$$

Finally the equation of the line 35 upon which the sound originates can be completely defined by determining the y-intercept b, which can be calculated as:

$$b = y' - mx' \qquad (Eq.\ 8)$$

The equation of the line 37 between E head 3-1 and the LLQ head 3-3 upon which the sound originated can be determined and in a similar fashion provides two equations and two unknowns. It is then possible to solve for the x and y coordinates of the intersection point 38 of lines 35 and 39 which represents the location 38 of the bowel sound. The intersection point 38 can be calculated using one of the several methods for solving simultaneous equations including the method published in "Software Spare Parts C Language Routines and Utilities" by Kent Porter (New American Library, New York and Scarborough, Ontario, ISBN 0-452-25840-5, p. 164). Repeating the above calculations for each sound defined in the sound tachograms creates the sound map.

The method and apparatus described herein for evaluating sounds originating in the gastrointestinal tract is easily integrated into current patient examination practice, is compatible with variations in equipment used by different physicians, is noninvasive and easy to implement, the accuracy is sufficient to minimize false positive and false negative results, and the time between the examination of the patient and the availability of the results is minimal.

While the invention has been described with reference to several particular embodiments thereof, those skilled in the art will be able to make the various modifications to the described embodiments of the invention without departing from the true spirit and scope of the invention. It is intended that all elements or steps which are insubstantially different or perform substantially the same function in substantially the same way to achieve the same result as what is claimed are within the scope of the invention. For example, the sound output from the patient's abdomen also could be produced from a group of devices including air-coupled condenser microphones, piezoelectric contact microphones and a variety of other microphones. The sound input could be initially input into a recording device other than a computer, such as a device belonging to the group of tape recorders, recorders using digital recording chips and other recorders that can make a record of the sound. The recorded sound may then be played back into the computer or otherwise converted into a digital sound file for analysis. The algorithm for the identification of bowel sounds could be accomplished using an alternative means of digitally processing the sound file belonging to the group of methods including using finite response digital filters, methods using fast fourier transforms, methods using wavelet analysis and other methods that allow the recognition of the bowel sound start and stop times. The filtering of the sound files to remove background noise can be accomplished using alternative methods belonging to the group of electronic circuits for high pass filtering, electronic circuits for low pass filtering, electronic circuits for band pass filtering and electronic circuits for other such types of signal processing to increase the signal to noise. Other metrics can be calculated from the sound files for basing a diagnosis which are in the group of the standard deviation of the average sound interval for the fasting patient, percentage of time involving bowel sounds in the fasting patient, etc. Furthermore, the metrics calculated can be used to diagnose other diseases belonging to the group of Crohn's disease, ulcerative colitis, duodenal ulcer, stomach ulcer, fecal incontinence and other gastrointestinal diseases. The metrics calculated can also be used to categorize those patients that are suspected of having non-ulcer dyspepsia into either a dysmotility group, which is very similar to irritable bowel syndrome patients, or into an ulcer like diathesis group. This distinction would be used to determine the type of medication that would be predicted to be most useful in that patient. A variety of other metrics may be calculated that distinguish between normal subjects and those with medical conditions, medical conditions other than irritable bowel syndrome may be diagnosed, the recording system could incorporate devices other than an electronic stethoscope for detecting sounds, the sounds could be initially recorded using a recorder other than the computer and a variety of different algorithms for detecting bowel sounds could be employed. The duration of time over which the bowel sounds are recorded could be more than or less than 2 minutes.

TABLE 1

```
HMMIOhmmio      //handle for wave file
DWORD     readsize,      //size for next read
HPSTR input,             //pointer to read bytes
DWORD     sum;           //summed data bytes
DWORD i;  //big enough counter to get through the input numbers
register int j;          //frequently used counter
int sample;
int       u;             //for message box
DWORD     dw;
CString errorMsg;
int *inArray,*fArray,*iA,*fA,*tA,*tempArray;
double *coeffc, *coeffd;
int w;
////variables for the IIR filter
double pi = 3.1415926535;
double a,b,sumc,sumd,cc[3],dd[2]; //values for filter
int m,n,jj,k,hifreq,lowfreq;      //boundary frequency in hz for band pass filter
hifreq = 450;
lowfreq = 200;
m=3
a=tan((double)((pi*lowfreq)(nsamplesPerSec));
b=tan((double)((pi*hifreq)/nSamplesPerSec));
cc[0]= -(b/((1+a)*(1+b)));
cc[1]=0;
cc[2]=-cc[0];
dd[0]=(((1+a)*(1-b))+((1-a)*(1+b)))/((1+a)*(1+b));
dd[1]=-(((1-a)*(1-b))/((1+a)*(1+b)));
input = (HPSTR)GlobalAllocPtr(GHND,readsize);   //allocate memory for read
```

TABLE 1-continued

```
if(!input) {
    errorMsg = "Error in allocating a buffer for input";
    goto cw_Error;        //make sure we got the memory
    }
dw = mmioRead(hmmio,input,readsize);        //read some data
if(dw == 0L)break;
tempArray = (int*)calloc(w-1,sizeof(int));    //array to hold overlap between segments
inArray = (int*)calloc(readsize,sizeof(int));  //array for "input" values--initialized to 0
fArray = (int*)calloc(readsize+(w-1),sizeof(int));//array for filtered values + overlap
iA = inArray;
fA = fArray;
/// fill inArray from input buffer
for (i=0;i<readsize;i++) {
    nuval = (int)(*input++);
    if(nuval !=0)
        nuval = (nuval>0)? nuval-128:nuval+129;
    *iA++ = nuval
    } //for fill in inArray
tA = tempArray;
for (i=0;i<(w-1);i++)        ////(add overlap values to fArray
    *fA++ =*tA++;
////filter the new values added to inArray
iA = inArray;
fA = fArray;
iA +=3
fA += (w-1);    //get to starting point in inArray leaving front padding
fA +=2;        //increment one more for filtering
for (n=3;n<readsize;n++) {
    sumc=sumd=0;
    coeffc = cc;
    coeffd = dd;
    for (k=0;k<m;k++) sumc += (*coeffc++)*(*iA--);
    for (jj=1;jj<m;jj++) sumd += (*coeffd++)*(*fA--);
    iA+=m+1;
    fA+=m;
    *fA = (int)(sumc+sumd);
    } ///for n
tA = tempArray;
fA = fArray;
fA += readsize; //set pointer to w-1 from end of array
for (i=0;i<(w-1);i++)    ////reassign tempArray to the last w-1 values of the filtered array
    *tA++ = *fA++;
////find peaks
fA = fArray;        //reset pointer
for (i=0;i<readsize;i++) { //recurse through all the values read
        sumAmplitude = 0;
        fA= fArray;
        fA +=i;
        for (j=0;j<w;j++) ////update array
            sumAmplitude += abs(*fA++);
        sumAmplitude/=w;
        if(tempstart == 0 && sumAmplitude >maxAmp) { //start a potential peak
            tempstart = (i+lastread);
            if(tempstart <=0) tempstart = 1; //when sound file starts with a sound
            maxsum = sumAmplitude;
        } //start a peak
        if(tempstart>0) if(sumAmplitude>maxsum)maxsum = sumAmplitude;
        if(sumAmplitude < maxAmp && tempstart >0) { //end of a potential peak]
            if((i+lastread)-tempstart > tcutoff) {//a valid length of peak
                cw_parms.peakstart[pcount]=tempstart;
                cw_parms.peakend[pcount]= (i+lastread);
                if(maxsum>32767) maxsum = 32700
                cw_parms.peakchanges[pcount] = (int)(maxsum);
            maxsum = 0;
                pcount++;
                //} //for merging peaks
            } //a valid peak
            tempstart=0;        //reset to search for new peak
        } //if peak
    } //for i
```

What is claimed is:

1. An apparatus for diagnosis of the presence or absence of irritable bowel syndrome in a patient, comprising:

(a) a first electronic microphone adapted to provide good acoustic contact with an abdomen of the patient;

(b) a medium adapted to communicate a signal produced by the first electronic microphone in response to bowel sounds in the patient to an analog-to-digital conversion circuit;

(c) a digital computer coupled to the analog-to-digital conversion circuit and adapted to receive therefrom digital information representative of a first sequence of bowel sounds of the patient in a fasting condition, and executing a program to i. produce a first group of digital numbers representing times of occurrence of fasting bowel sounds having at least a first predetermined amplitude, and store the first group of digital numbers as a first tachogram, and ii. compute a first number representative of a frequency of the fasting bowel sounds from the first tachogram, to indicate a diagnosis of irritable bowel syndrome in the patient if the first number bears a predetermined relationship to a predetermined threshold.

2. The apparatus of claim 1 wherein the first number is a sound-sound interval associated with the fasting bowel sound.

3. The apparatus of claim 2 wherein the sound-sound interval is less than approximately 640 milliseconds.

4. The apparatus of claim 1 wherein the digital computer is adapted to receive digital information representative of a second sequence of bowel sounds of the patient in a fed condition from the analog-to-digital conversion circuit, and executes a program to produce a second group of digital numbers representing times of occurrence of fed bowel sounds having at least a second predetermined amplitude and store the second group of digital numbers as a second tachogram, compute a second number representative of a frequency of the fed bowel sounds, and compute a first ratio representative of a predetermined relationship between the first number and the second number, to thereby indicate the diagnosis of irritable bowel syndrome in the patient if the ratio bears a predetermined relationship to a predetermined threshold.

5. The apparatus of claim 1 wherein the computer is a personal computer and the analog-to-digital conversion circuit includes a sound card connected to the computer.

6. The apparatus of claim 5 wherein the medium includes an electronic cable.

7. The apparatus of claim 1 wherein the electronic microphone is included in an electronic stethoscope.

8. The apparatus of claim 1 wherein the computer executes the program to filter the data in the first group of digital numbers using an infinite impulse response bandpass filter to provide a pass band between approximately 200 and 450 Hertz to produce a sequence of filtered sound amplitudes.

9. The apparatus of claim 8 wherein the computer executes the program to generate bowel sound start times and bowel sound stop times of presumed bowel sounds to generate the first tachogram.

10. The apparatus of claim 9 wherein the computer executes the program to compute a sound-sound interval representative of the frequency of the presumed bowel sounds.

11. The apparatus of claim 1 including a frame supporting the first electronic microphone and second and third electronic microphones, the medium connecting the analog-to-digital conversion circuit to the second and third electronic microphones, and wherein the computer operates the program to determine the locations of the bowel sounds by triangulation computations on data of the first tachogram and second and third tachograms produced, simultaneously with the first tachogram, in response to the second and third electronic microphones, respectively.

12. The apparatus of claim 11 wherein the computer operates the program to indicate a diagnosis based on the determined locations of the bowel sounds.

13. The apparatus of claim 1 including a sound-conducting gel on the first electronic microphone to transmit sound energy from the abdomen to the first electronic microphone.

14. The apparatus of claim 10 wherein the computer operates the program to determine if each presumed bowel sound represented in the first tachogram is a valid bowel sound by computing a power spectra for non-filtered digital data between the start time and stop time for each presumed bowel sound represented in the first tachogram and deleting each presumed bowel sound from the first tachogram if at least a predetermined portion of its power spectra is not between approximately 200 and 450 Hertz.

15. The apparatus of claim 14 wherein the predetermined portion is 15 percent.

16. A method for diagnosis of the presence or absence of irritable bowel syndrome in a patient, comprising:

(a) providing a first electronic microphone adapted to provide good acoustic contact with an abdomen of the patient;

(b) converting a signal produced by the first electronic microphone in response to bowel sounds in the patient to a time sequence of digital numbers representing the bowel sounds;

(c) operating a computer to process a first time sequence of the digital numbers representing the first time sequence of bowel sounds of the patient in a fasting condition;

(d) operating the computer to produce a first group of digital numbers representing times of occurrence of fasting bowel sounds having at least a first predetermined amplitude and store the first group of digital numbers as a first tachogram;

(e) operating a computer to compute a first number representative of a frequency of the fasting bowel sounds from the first tachogram; and (f) indicating a diagnosis of irritable bowel syndrome in the patient if the first number bears a predetermined relationship to a predetermined threshold.

17. The method of claim 16 wherein the first number is a sound-sound interval associated with the fasting bowel sound.

18. The method of claim 17 wherein the sound-sound interval is less than approximately 640 milliseconds.

19. The method of claim 16 including filtering the first time sequence of numbers using an infinite impulse response bandpass filter to provide a pass band between approximately 200 and 450 Hertz to produce a sequence of filtered sound amplitudes.

20. The method of claim 19 wherein the computer executes the program to generate bowel sound start times and bowel sound stop times of presumed bowel sounds to generate the first tachogram.

21. The method of claim 20 wherein the computer executes the program to compute a sound-sound interval representative of the frequency of the presumed bowel sounds.

22. The method of claim 16 including supporting the first electronic microphone and second and third electronic microphones in acoustic contact with the abdomen, and computing second and third tachograms from the bowel sounds detected by the second and third electronic microphones, respectively, simultaneously with the computing of the first tachogram, and computing the locations of the bowel sounds by triangulation from data representative of the locations of the first, second, and third electronic microphones and intensities of bowel sound signals received from the first, second, and third electronic microphones.

23. The method of claim 16 including providing a sound-conducting gel on the first electronic microphone to transmit sound energy from the abdomen to the first electronic microphone.

24. The method of claim 21 operating the computer to determine if each presumed bowel sound represented in the first tachogram is a valid bowel sound by computing a power spectra for non-filtered digital data between the start time and stop time for each presumed bowel sound represented in the first tachogram and deleting each presumed bowel sound from the first tachogram if at least a predetermined portion of its power spectra is not between approximately 200 and 450 Hertz.

25. The method of claim 24 wherein the predetermined portion is 15 percent.

26. The method of claim 16 including digital information representative of a second sequence of bowel sounds of the patient in a fed condition from the analog-to-digital conversion circuit, and executes a program to produce a second group of digital numbers representing times of occurrence of fed bowel sounds having at least a second predetermined amplitude and store the second group of digital numbers as a second tachogram, compute a second number representative of a frequency of the fed bowel sounds, compute a first ratio representative of a predetermined relationship between the first number and the second number, and produce the diagnosis of irritable bowel syndrome in the patient if the ratio bears a predetermined relationship to a predetermined threshold.

27. A method for diagnosis of the presence or absence of irritable bowel syndrome in a patient, comprising:
    (a) providing a first electronic microphone adapted to provide good acoustic contact with an abdomen of the patient;
    (b) in response to bowel sounds received by the microphone, determining periods of bowel sound signals of at least a predetermined average level; and
    (c) indicating a diagnosis of irritable bowel syndrome in the patient if a predetermined relationship exists between the intervals.

28. The method of claim 27 wherein the predetermined relationship is that the average time between periods is less than a predetermined amount.

29. The method of claim 28 wherein the predetermined amount is approximately 640 milliseconds.

30. The method of claim 27 including filtering a bowel sound signal representative of a signal produced by the first electronic microphone in response to bowel sounds in the patient.

31. The method of claim 30 wherein the filtering includes filtering components of the bowel sound signal outside of a pass band between approximately 200 and 450 Hertz.

32. The method of claim 28 including prescribing a medication consistent with treatment of irritable bowel syndrome if the average time is less than the predetermined amount.

33. The method of claim 28 including prescribing a medication consistent with an ailment other than irritable bowel syndrome if the average time is greater than the predetermined amount.

34. A method for diagnosis of the presence or absence of irritable bowel syndrome in a patient, comprising:
    (a) providing a first electronic microphone adapted to provide good acoustic contact with an abdomen of the patient;
    (b) filtering an output signal produced by the microphone in response to bowel sounds received by the microphone to eliminate background noise therefrom;
    (c) in response to the filtered output signal, determining sound-sound intervals of bowel sound signals having at least a predetermined average level; and
    (e) indicating a diagnosis of irritable bowel syndrome in the patient if an average of the sound-sound intervals is less than a predetermined value.

35. The method of claim 34 wherein the predetermined value is approximately 640 milliseconds.

36. A method for diagnosis of the presence or absence of irritable bowel syndrome in a patient, comprising:
    (a) providing a first electronic microphone adapted to provide good acoustic contact with an abdomen of the patient;
    (b) filtering an output signal produced by the microphone in response to bowel sounds received by the microphone to eliminate background noise therefrom;
    (c) determining which filtered output signals produced by the microphone are valid bowel sound signals by computing a power spectra of the filtered output signals and determining which of them have at least a predetermined percentage of their power spectra within a predetermined range of frequencies;
    (d) determining sound-sound intervals of the valid bowel sound signals having at least a predetermined average level; and
    (e) indicating a diagnosis of irritable bowel syndrome in the patient if an average of the sound-sound intervals is less than a predetermined value.

37. The method of claim 36 wherein the predetermined range of frequencies is the range between approximately 200 Hz and 450 hertz.

38. The method of claim 37 wherein the predetermined percentage is approximately 15 percent.

39. A method for diagnosis of the presence or absence of a bowel dysfunction in a patient, comprising:
    (a) providing a first electronic microphone adapted to provide good acoustic contact with an abdomen of the patient;
    (b) filtering an output signal produced by the microphone in response to bowel sounds received by the microphone to eliminate background noise therefrom;
    (c) in response to the filtered output signal, determining sound-sound intervals of bowel sound signals having at least a predetermined average level; and
    (d) indicating a diagnosis of the bowel dysfunction in the patient if a predetermined relationship exists between the sound-sound intervals.

40. A method for providing an amplitude-independent characterization of bowel sounds produced by a patient, comprising:
    (a) providing a first electronic microphone adapted to provide good acoustic contact with an abdomen of the patient;
    (b) filtering an output signal produced by the microphone in response to sounds received by the microphone to eliminate background noise therefrom;
    (b) selecting sound signals from the filtered output signal which have at least a predetermined amplitude and a predetermined duration;
    (c) in response to the filtered output signal, determining sound-sound intervals of bowel sound signals of at least a predetermined average level; and (d) selecting sound signals which constitute valid bowel sounds by computing a power spectra of sound signals determined according to step (c) and selecting the sound signals which have at least a predetermined percentage of their power spectra within a predetermined range of frequencies.

* * * * *